US00RE42718E

(19) United States
(12) Reissued Patent
Yan et al.

(10) Patent Number: US RE42,718 E
(45) Date of Reissued Patent: Sep. 20, 2011

(54) CRUDE EXTRACTS FROM ANDROGRAPHIS PANICULATA

(75) Inventors: Xiaoqiang Yan, Shanghai (CN); Tao Wang, Shanghai (CN); Zhiming Ma, Suzhou (CN); Weihan Zhang, Shanghai (CN); Jifeng Duan, Shanghai (CN); Yu Cai, Shanghai (CN)

(73) Assignee: Hutchison Medipharma Enterprises Limited, Nassau, New Providence (BS)

( * ) Notice: This patent is subject to a terminal disclaimer.

(21) Appl. No.: 12/717,260

(22) Filed: Mar. 4, 2010

Related U.S. Patent Documents

Reissue of:
(64) Patent No.: 7,341,748
Issued: Mar. 11, 2008
Appl. No.: 11/116,678
Filed: Apr. 27, 2005

U.S. Applications:
(60) Provisional application No. 60/566,477, filed on Apr. 28, 2004.

(51) Int. Cl.
*A61K 36/00* (2006.01)
(52) U.S. Cl. ..... 424/725
(58) Field of Classification Search ..... None
See application file for complete search history.

(56) References Cited

U.S. PATENT DOCUMENTS

| | | | |
|---|---|---|---|
| 6,358,526 | B1 | 3/2002 | Mergens et al. |
| 7,341,748 | B2 | 3/2008 | Yan et al. |
| 7,625,945 | B2 | 12/2009 | Yan et al. |
| 2002/0068098 | A1 | 6/2002 | Babish et al. |
| 2003/0059471 | A1 | 3/2003 | Compton et al. |
| 2003/0091517 | A1 | 5/2003 | Rojanapanthu et al. |
| 2003/0101076 | A1 | 5/2003 | Zaleski |
| 2003/0104076 | A1 | 6/2003 | Berkulin et al. |
| 2004/0053858 | A1 | 3/2004 | Berg |
| 2004/0151792 | A1 | 8/2004 | Tripp et al. |
| 2005/0215628 | A1 | 9/2005 | Yan et al. |
| 2006/0246156 | A1 | 11/2006 | Yan et al. |
| 2007/0202164 | A1 | 8/2007 | Wang et al. |
| 2007/0218114 | A1 | 9/2007 | Duggan et al. |
| 2009/0117209 | A1 | 5/2009 | Duan et al. |
| 2009/0117210 | A1 | 5/2009 | Duan et al. |

FOREIGN PATENT DOCUMENTS

| | | | |
|---|---|---|---|
| CN | 1042077 | | 5/1990 |
| CN | 148 837 6 | | 4/2004 |
| CN | 1626076 | A | 6/2005 |
| CN | 1628764 | A | 6/2005 |
| JP | 2000-034233 | | 2/2000 |
| JP | 2001-058969 | A | 3/2001 |
| JP | 2001-58969 | A * | 3/2001 |
| JP | 2001058969 | | 3/2001 |
| JP | 2004-75638 | | 3/2004 |
| KR | 1020050067951 | A | 7/2005 |
| WO | WO 2005/104722 | A2 | 11/2005 |
| WO | WO 2007/098686 | A1 | 9/2007 |
| WO | WO 2009/059158 | A1 | 5/2009 |

OTHER PUBLICATIONS

Hasko (Immunology (2001), vol. 103, pp. 473-478).*
Achike et al., "Nitric Oxide, Human Diseases and the Herbal Products that Effect the Nitric Oxide Signalling Pathway," *Clinical & Experimental Pharmacology & Physiology,* 30: 605-615 (2003).
Akbarsha et al., "Antifertility effect of *Andrographis paniculata* (nees) in male albino rat," *Indian Journal of Experimental Biology,* 28:421-426 (1990).
Balmain et al., "Minor Diterpenoid Constituents of *Andrographis paniculata* Nees," *J. Chem. Soc. Perkin. Trans. I* (1973): 1247-1251.
Basak et al., "Implication of the protein convertases furin, PC5 and PC7 in the cleavage of surface glycoproteins of Hong Kong, Ebola and respiratory syncytial viruses: a comparative analysis with fluorogenic peptides," *Biochem J.,* 353:537-545 (2001).
Burgos et al., "Testicular toxicity assessment of *Andrographis paniculata* dried extract in rats," *J. Ethnopharmacol.,* 58(3): 219-224 (1997).
Calabrese et al., "A Phase I Trial of Andrographolide in HIV Positive Patients and Normal Volunteers," *Phytother. Res.,* 14:333-338 (2000).
Chang et al., "Dehydroandrographolide succinic acid monoester as an inhibitor against the human immunodeficiency virus," *Proc. Soc. Exp. Biol. Med.,* 197(1): 59-66 (1991).
Chen et al., "Nine new ent-labdane diterpenoids from the aerial parts of *Andrographis paniculata," Helvetica Chimica Acta,* 89:2654-2664 (2006).
Chen et al. , "Studies on flavonoids of *Andrographis paniculata," China J. Chinese Materia Medica.,* 31(5):391-395 (2006).
Chen et al., "Studies on diterpenoids from *Andrographis paniculata," China J. Chinese Materia Medica.,* 31(19):1594-1597 (2006).
Coon et al., "*Andrographis paniculata* in the Treatment of Upper Respiratory Tract Infections: A Systematic Review of Safety and Efficacy," *Planta Med.,* 70(4): 293-298 (2004).
Deng et al., *Chinese Pharm. Bull.,* 17:195-198 (1982).

(Continued)

*Primary Examiner* — Susan Hoffman
(74) *Attorney, Agent, or Firm* — Finnegan, Henderson, Farabow, Garrett & Dunner, LLP

(57) ABSTRACT

This invention relates to a method of inhibiting TNFα or IL-1β expression with an extract of Andrographis paniculata. The extract contains andrographolide, 14-deoxy-andrographolide, 14-deoxy-11,12-dehydrogen-andrographolide, and neoandrographolide.

11 Claims, No Drawings

OTHER PUBLICATIONS

Fujita et al., "On the diterpenoids of *Andrographis paniculata:* x-ray Crystallographic analysis of andrographolide and structure determination of new minor diterpenoids," *Chem. Pharm. Bull.,* 32(6):2117-2125 (1984).
George et al., "Investigations on plant antibiotics. Part IV. Further search for antibiotic substances in Indian medicinal plants," *Indian Journal of Medical Research,* (37): 169-181 (2004).
Ghosh et al., "Isolation of *Andrographis paniculata* leaf protein with antifungal property," *Acto. Phytopathologica et Entomologica Hungarica,* 39(4):377-381 (2004).
Gupta et al., "Flavonoids of *Andrographis paniculata," Phytochemistry,* 22(1):314-315 (1983).
Gupta et al., "Antidiarrheal activity of diterpenes of *Andrographis paniculata* (kalmegh) against *Escherichia coli* enterotoxin in in vivo models," *International Journal of Crude Drug Research,* (28): 273-283 (1990).
Gupta et al., "Antisecretory (antidiarrhoeal) activity of Indian medicinal plants against *Escherichia coli* enterotoxin-induced secretion in rabbit and guinea pig ileal loop models," *Inl. J, Pharmacog.,* 31(3):198-204 (1993).
Gupta et al., "Flavonoid glycoside of *Andrographis paniculata," Indian J. Chem.,* 35 B:512-513 (1996).
Habtemariam, "Andrographolide inhibits the tumour necrosis Factor-α-induced upregulation of ICAM-1 expression and endothelial-monocyte adhesion," *Phytotherapy Research,* 12:37-40 (1998).
Habtemariam, "Natural Inhibitors of Tumor Necrosis Factor-α Production, Secretion and Function," *Planta Medica,* 66:303-313 (2000).
Herbs, *Andrographis paniculata's wide range of medicinal Powers,* (2002).
Jalal et al., "Formation of three new Flavones by differentiating callus cultures of *Andrographis paniculata," Phytochemistry,* 18:149-151 (1979).
Jantan et al., "Ent-14β-Hydroxy-8(17),12-Labdadien-16,15-Olide-3β,19 Oxdide: a Diterpene from the aerial parts of *Andrographis paniculata," Phytochemistry,* 37(5):1477-1479 (1994).
Kakrani et al., "Traditional treatment of gastro-intestinal tract disorders in Kutch district, Gujarat state, India," *Journal of Natural Remedies,* 2/1: 71-75 (2002).
Kleipool, "Constituents of *Andrographis paniculata nees," Nature,* 169(4288):33-34 (1952).
Kumar et al., "Anticancer and immunomodulatory potential of DRF-3188, an analogue of andrographolide," *Novel Compounds from Natural Products in ihe New Millenium,* 205-216, (2004). (Abstract).
Madav et al., "Analgesic, antipyretic and antiulcerogenic effects of andrographolide," *Indian J. Pharm. Sci.,* 57(3):121-125 (1995).
Madav et al., "Anti-inflammatory activity of andrographolide," *Fitoterapia,* 67:452-458, (1996).
Mahadevan et al., "Safety of selective cyclooxygenase-2 inhibitors in inflammatory bowel disease," *Am. J. Gastroenterology,* 97(4): 910-4 (2002) (Abstract).
Matsuda et al., "Studies on the cell differentiation induces of Andrographis paniculata," *Tennen Yuki Kagobutsu Toronkai Koen Yoshishu,* 33:433-440 (1991) (Abstract).
Matsuda et al., "Cell differentiation-inducing diterpenes from *Andrographis paniculata Nees," Chem. Pharm. Bull.,* 42(6):1216-1225 (1994).
Mishra et al., "*Andrographis paniculata* (Kalmegh): A Review," *Pharmacognosy Reviews,* 1(2):283-298 (2007).
Misra et al., "Antimalarial activity of traditional plants against erythrocytic stages of *Plasmodium berghei," International Journal of Pharmacognosy,* (29): 19-23 (1991).
Nazimudeen et al., "Effect of Andrographis paniculata on snake venom-induced death and its mechanism," *Indian Journal of Pharmaceutical Sciences,* (40):132-133 (1978).
Otake et al., "Screening of Indonesian plant extracts for anti-human immunodeficiency virus type 1 (HIV-1) activity," *Phytotherapy Research,* (9): 6-10 (1995).
Panossian et al., "Effect of *Andrographis paniculata* extract on progesterone in blood plasma of pregnant rats," Phytomedicine, 6(3):157-161 (1999). (Abstract).
Panossian et al., "Effect of andrographolide and Kan Jang—fixed combination of extract SHA-10 and extract SHE-3 -on proliferation of human lymphocytes, production of cytokines and immune activation markers in the whole blood cells culture," *Phytomedicine,* 9(7):598-605 (2002). (Abstract).
Peng et al., "Modulation of Lianbizi injection (andrographolide) on some immune functions," *Zhongguo Zhongyao Zazhi,* 27(2):147-150 (2002) (Abstract).
Poolsup et al., "*Andrographis paniculata* in the symptomatic treatment of uncomplicated upper respiratory tract infection: systematic review of randomized controlled trials," *J. Clin. Pharm. Ther.,* 29(1): 37-45 (2004).
Pramanick et al., "Andropanolide and isoandrographolide, minor diterpenoids from *Andrographis paniculata:* structure and X-ray crystallographic analysis," *J. Nat. Prod.,* 69: 403-405 (2006).
Puri et al., "Immunostimulant agents from *Andrographis Paniculata," Journal of National Products,* 56(7):995-999 (1993).
Qian et al., "A comparison of pharmacological effects between CXL extract and CXL compound prescription," *Journal of Luzhou Medical School,* 11(3): 189-191 (1988).
Rajagopal et al., "Andrographolide, a potential cancer therapeutic agent isolated from Andrographis paniculata," *Journal of Experimental Therapeutics and Oncology,* 3(3):147-158 (2003). (Abstract).
Rao et al., "Flavonoids and andrographolides from *Andrographis paniculata," Phytochemistry,* 65(16):2317-2321 (2004). (Abstract).
Reddy et al., "A flavone and an unusual 23-carbon terpenoid from *Andrographis paniculata," Phytochemistry,* 62:1271-1275 (2003).
Reddy et al., "A new BIS-Andrographolide ether from *Andrographis paniculata* Nees and evaluation of anti-HIV activity," *Natural Product Research,* 19(3):223-230 (2005).
Saxena et al., "Phytochemicals from *Andrographis paniculata," Indian J. Chem.,* 42B:3159-3163 (2003).
See et al., "Increased tumor necrosis factor alpha (TNF-. alpha.) and natural killer cell (NK) function using an integrative approach in late stage cancers," *Immunological Investigations,* 31(2):137-153 (2002). (Abstract).
Shen et al., "Andrographolide prevents oxygen radical production by human neutrophils: possible mechanism(s) involve in its anti-inflammatory effect," *British Journal of Pharmacology,* 135:399-406 (2002).
Shen et al., "*ent*-Labdane diterpenoids from *Andrographis paniculata," J. Nat. Prod.,* 69:319-322 (2006).
Singha at al., "Antimicrobial activity of Andrographis paniculata," *Fitoterapia,* 74:692-694 (2003).
Thamaree et al., "The effect of andrographolide on the production of proinflammatory cytokines by in vitro stimulated human blood cells," *Inflammation Res.,* 46, Suppl. 3, S224, (1997). (Abstract).
Townsend et al., "Extracts of Chinese Herbs Inhibit IL-Ibeta- and UV-induced MMP Expression in Cultured Human Keratinocytes," *FASEB Journal,* 15(4): A184 (2001).
Trivedi et al., "Hepatoprotective and antioxidant property of Andrographis paniculata (Nees) in BHC induced liver damage in mice," *Indian J. Exp. Biol.,* 39(1):41-6 (2001). (Abstract).
Vedavathy et al., "Antipyretic activity of six indigenous medicinal plants of Tirumala Hills, Andhra Pradesh, India," *Journal of Ethnopharmacology,* 33(1-2): 193-196 (1991).
Wang et al., "A Discussion on the effect of the extraction process of Chinese traditional medicine on the quality of the resulting drug," Heilongjiang Chinese Medicine, No. 2: 45-46 (1992).
Wang et al., "Andrographolide reduces inflammation-mediated dopaminergic neurodegeneration in mesencephalic neuron-glia cultures by inhibiting microglial activation," *Journal of Pharmacology and Experimental Therapeutics,* 308(3):915-983 (2004) (Abstract).
Wang et al., "Chemical constituents from leaves of *Andrographis paniculata," J. China Pharma. Univ.,* 36(5):405-407 (2005).
Xia, "Andrographolide Attenuates Inflammation by Inhibition of NF-κB Activation Through Covalent Modification of Reduced Cysteine 62 of p50[1]," *The Journal of Immunology,* 4207-4217 (2004).

Yao et al., "Mechanism of inhibition of HIV-1 infection in vitro by a purified extract of *Prunella vulgaris," Virology,* 187(1): 56-62 (1992).
Zhang et al., "Effects of 14-Deoxyandrographolide and 14-Deoxy-11,12-Didehydroandrographolide on Nitric Oxide Production in Cultured Human Endothelial Cells," *Phytotherapy Research,* 13:157-159 (1999).
Zhang et al., "Experimental Studies of the destructive actions of *Andrographis paniculata* nees on endotoxin in vitro," *Chinese J. of Integrated Traditional and Western Medicine in Intensive and Critical Care,* 7(4):212-214 (2000).
Zhang et al., "Antihyperglycaemic and anti-oxidant properties of *andrographis paniculata* in normal and diabetic rats," *Clinical and Experimental Pharmacology and Physiology,* 27:358-363 (2000).
Zhang et al., "New Diterpenoids from *Andrographis paniculata* (Burm. f.) nees," *J. of Integrative Plant Biology,* 48(9): 1122-1125 (2006).
Zhong et al., "Three salts of labdanic acids from *Andrographis paniculata* (Acanthaceae)," *Acta Botanica Sinica,* 43:1077-1080 (2001).
Zhou et al., "Two new *ent*-labdane diterpenoid glycosides from the aerial parts of *Andrographis paniculata," Journal of Asian Natural Products Research,* 10(10):939-943 (2008).
Andrographis Paniculata Tablets, *The Pharmacopoeia of People's Republic of China* (2000 ed.), Vol. I, p. 541 (2000).
Andrographis Paniculata Tablets, *The Pharmacopoeia of People's Republic of China* (2005 ed.), Vol. I, pp. 549-550 (2005).
*Guidance for Industry Botanical Drug Products,* U.S. Department of Health and Human Services Food and Drug Administration, Center for Drug Evaluation and Research (CDER), Jun. 2004.
*Practical Techniques for National Qualification Examination of Professional Skills in Chinese medication,* Professional Skills, Shanghai Science and Technology Press, China, p. 164 (2003).
Herba Andrographis, *World Health Organization* (*WHO*) *monographs on selected medicinal plants,* Vol. 2. pp. 12-24 (2002).
Office Action mailed Jul. 7, 2008, in U.S. Appl. No. 11/934,143.
Amendment in Reply to Non-Final Office Action of Jul. 7, 2008 with Exhibits A & B, filed Nov. 7, 2008, in U.S. Appl. No. 11/934,143.
Final Office Action mailed Mar. 20, 2009, in U.S. Appl. No. 11/934,143.
Amendment and Reply Under 37 C.F.R. § 1.114 filed Sep. 18, 2009, in U.S. Appl. No. 11/934,143.
Office Action mailed Dec. 15, 2009, in U.S. Appl. No. 11/934,143.
Reply to Office Action filed Mar. 15, 2010, in U.S. Appl. No. 11/934,143.
Office Action mailed Aug. 1, 2006, in U.S. Appl. No. 11/116,678.
Amendment in Reply to Action of Aug. 1, 2006 filed Dec. 1, 2006, in U.S. Appl. No. 11/116,678.
Final Office Action mailed Feb. 21, 2007, in U.S. Appl. No. 11/116,678.
Reply to Action of Feb. 21, 2007 with Exhibit A, filed May 21, 2007, in U.S. Appl. No. 11/116,678.
Office Action mailed Jun. 2, 2009, in U.S. Appl. No. 11/674,557.
Reply to Office Action filed Oct. 1, 2009, in U.S. Appl. No. 11/674,557.
Final Office Action mailed Jan. 4, 2010, in U.S. Appl. No. 11/674,557.
PCT Notification of Transmittal of the International Search Report and the Written Opinion of the International Searching Authority, mailed Sep. 13, 2006, in International Application No. PCT/US2005/008317.
PCT Notification of Transmittal of the International Search Report and the Written Opinion of the International Searching Authority, or the Declaration, mailed Jun. 7, 2007, in International Application No. PCT/CN2007/000616.
PCT International Preliminary Report on Patentability issued Sep. 2, 2008, in International Application No. PCT/CN2007/000616.
PCT Notification of Transmittal of the International Search Report and the Written Opinion of the International Searching Authority, or the Declaration, mailed Jan. 26, 2009, in International Application No. PCT/US2008/082022.
PCT Notification of Transmittal of the International Search Report and the Written Opinion of the International Searching Authority, or the Declaration, mailed Dec. 9, 2005, in International Application No. PCT/US05/14288.
PCT International Preliminary Report on Patentability mailed Nov. 9, 2006, in International Application No. PCT/US2005/14288.
Assche et al., "Daclizumab, a humanised monoclonal antibody to the interleukin 2 receptor (CD25), for the treatment of moderately to severely active ulcerative colitis: a randomised, double blind, placebo controlled, dose ranging trial," *Gut* 55;1568-1574 (2006).
Feagan et al., "Omega-3 Free Fatty Acids for theMaintenance of Remission in Crohn Disease," *JAMA,* 299(14):1690-1697 (2008).
Rutgeerts et al., "Onercept for Moderate-to-Severe Crohn's Disease: A Randomized, Double-Blind, Placebo-Controlled Trial," Clinical Gastroenterology and Hepatology, 4:888-893 (2006).
Sandborn et al., "Anti-CD3 antibody visilizumab is not effective in patients with intravenous corticosteroid-refractory ulcerative colitis," *Gut,* 59: 1485-1492 (2010).
Tang et al., "Herbal extract HMPL-004 in Active Ulcerative Colitis: A Randomized Comparison with Sustained Release Mesalamine," American Journal of Gastroenterology (2010).
Pre-IND Submission Meeting Briefing Document (Redacted) (2005).
Slide presented to FDA in Jul. 2010.
Communication pursuant to Rule 114(2) EPC in EP1996165, dated Apr. 29, 2010, enclosing Third Party Observations.
William J. Sandborn, "Declaration of William J. Sandborn, M.D., under 37 C.F.R. § 1.132" with Exhibit 1, filed on Dec. 15, 2010, in U.S. Appl. No. 11/934,143.
Jianguo Ji, "Declaration under 37 C.F.R. § 1.132" with Exhibits 1-4, filed on Dec. 15, 2010, in U.S. Appl. No. 11/934,143.
Jifeng Duan, "Declaration under 37 C.F.R. § 1.132," filed on Dec. 15, 2010, in U.S. Appl. No. 11/934,143.
Li Wang, "Declaration under 37 C.F.R. § 1.132," filed on Dec. 15, 2010, in U.S. Appl. No. 11/934,143.
Zhiming Ma, "Declaration under 37 C.F.R. § 1.132," filed on Dec. 15, 2010, in U.S. Appl. No. 11/934,143.
Tao Wang, "Declaration under 37 C.F.R. § 1.132," filed on Dec. 15, 2010, in U.S. Appl. No. 11/934,143.
Weihan Zhang, "Declaration under 37 C.F.R. § 1.132," filed on Dec. 15, 2010, in U.S. Appl. No. 11/934,143.
Weihan Zhang, "First Declaration under 37 C.F.R. § 1.132," filed on Dec. 15, 2010, in U.S. Appl. No. 11/934,143.
Weihan Zhang, "Second Declaration under 37 C.F.R. § 1.132," filed on Dec. 15, 2010, in U.S. Appl. No. 11/934,143.
Xiaoqiang Yan, "Declaration under 37 C.F.R. § 1.132," filed on Dec. 15, 2010, in U.S. Appl. No. 11/934,143.
Xun Zhang, "Declaration under 37 C.F.R. § 1.132," filed on Dec. 15, 2010, in U.S. Appl. No. 11/934,143.
Yu Cai, "Declaration under 37 C.F.R. § 1.132," filed on Dec. 15, 2010, in U.S. Appl. No. 11/934,143.
Yuqing Wang, "Declaration under 37 C.F.R. § 1.132," filed on Dec. 15, 2010, in U.S. Application No. 11/934,143.
Jianguo Ji, "Declaration under 37 C.F.R. § 1.132" with Exhibits 1, dated Dec. 20, 2010.
Weihan Zhang, "First Declaration under 37 C.F.R. § 1.132," dated Dec. 21, 2010.
Weihan Zhang, "Second Declaration under 37 C.F.R. § 1.132," dated Dec. 21, 2010.
*Ex parte Subramanyam* (BPAI, Mar. 29, 2010).
Final Office Action mailed Jun. 16, 2010, in U.S. Appl. No. 11/934,143.
Amendment and Reply under 37 U.S.C. § 1.114, in U.S. Appl. No. 11/934,143, filed Dec. 15, 2010.
Office Action mailed Jun. 16, 2010, in U.S. Appl. No. 11/674,557.
English translation of JP 2000034233 A—2000.*

* cited by examiner

CRUDE EXTRACTS FROM ANDROGRAPHIS PANICULATA

Matter enclosed in heavy brackets [ ] appears in the original patent but forms no part of this reissue specification; matter printed in italics indicates the additions made by reissue.

CROSS REFERENCE TO RELATED APPLICATIONS

Pursuant to 35 USC § 119(e), this application claims priority to U.S. Provisional Application Ser. No. 60/566,477, filed Apr. 28, 2004, the contents of which are incorporated herein by reference.

BACKGROUND

Tumor Necrosis Factor alpha (TNF-α), a mononuclear cytokine, is predominantly produced by monocytes and macrophages. It possesses various biological activities: (1) killing cancer cells or inhibiting growth of cancer cells, (2) enhancing phagocytosis of neutrophilic granulocyte, (3) killing infectious pathogens, and (4) increasing expression of adhesion molecules on vascular endothelial cells during inflammatory responses. Disorders related to expression of TNF-α include, but are not limited to, rheumatoid arthritis, juvenile rheumatoid arthritis, osteoarthritis, spondyloarthropathies, inflammatory bowel disease (including Crohn's disease and ulcerative colitis), chronic heart failure, systemic lupus erythematosus, scleroderma, sarcoidosis, polymyositis/dermatomyositis, psoriasis, multiple myeloma, myelodysplastic syndrome, acute myelogenous leukemia, Parkinson's disease, AIDS dementia complex, Alzheimer's disease, depression, sepsis, pyoderma gangrenosum, hematosepsis, septic shock, Behcet's syndrome, graft-versus-host disease, uveitis, Wegener's granulomatosis, Sjogren's syndrome, chronic obstructive pulmonary disease, asthma, acute pancreatitis, periodontal disease, cachexia, central nervous system injury, cancer (e.g., lung carcinomas, esophagus carcinoma, gastric adenocarcinoma, and prostate carcinoma), viral respiratory disease, and obesity. See, e.g., Ogata H. et al Curr Pharm Des. 2003; 9(14): 1107-13; Moller D. R. et al J Intern Med. 2003; 253(1): 31-40; Taylor P. C. et al Curr Pharm Des. 2003; 9(14): 1095-106; Wilkinson N. et al Arch Dis Child. 2003; 88(3): 186-91; Nishimura F. et al J Periodontol. 2003; 74(1): 97-102; Weinberg J. M. et al Cutis. 2003; 71(1): 41-5; Burnham E. et al Crit Care Med. 2001; 29(3): 690-1; Sack M. et al Pharmacol Ther. 2002; 94(1-2): 123-35; Barnes P. J. et al Annu Rev Pharmacol Toxicol. 2002; 42:81-98; Mageed R. A. et al Lupus 2002; 11(12): 850-5; Tsimberidou A. M. et al Expert Rev Anticancer Ther. 2002; 2(3): 277-86; Muller T. et al Curr Opin Investig Drugs. 2002; 3(12): 1763-7; Calandra T. et al Curr Clin Top Infect Dis. 2002; 22:1-23; Girolomoni G et al Curr Opin Investig Drugs. 2002; 3(11): 1590-5; Tutuncu Z. et al Clin Exp Rheumatol. 2002; 20(6 Suppl 28): S146-51; Braun J. et al Best Pract Res Clin Rheumatol. 2002; 16(4): 631-51; Barnes P. J. et al Novartis Found Symp. 2001; 234: 255-67; discussion 267-72; Brady M. et al Baillieres Best Pract Res Clin Gastroenterol. 1999; 13(2): 265-89; Goldring M. B. et al Expert Opin Biol Ther. 2001; 1(5): 817-29; Mariette X. Rev Prat. 2003; 53(5): 507-11; Sharma R. et al Int J Cardiol. 2002; 85(1): 161-71; Wang C. X. et al Prog Neurobiol. 2002; 67(2): 161-72; Van Reeth K. et al Vet Immunol Immunopathol. 2002; 87(3-4): 161-8; Leonard B. E. et al Int J Dev Neurosci. 2001; 19(3): 305-12; and Hays S. J. et al Curr Pharm Des. 1998; 4(4): 335-48.

Interleukin-1 beta (IL-1β), a cytokine secreted by cells such as monocytes, macrophages and dendritic cells, mediates a wide range of immune and inflammatory responses. One can modulate IL-1β production to treat a variety of disorders, such as rheumatoid arthritis, hematosepsis, periodontal disease, chronic heart failure, polymyositis/dermatomyositis, acute pancreatitis, chronic obstructive pulmonary disease, Alzheimer's disease, osteoarthritis, bacterial infections, multiple myeloma, myelodysplastic syndrome, uveitis, central nervous system injury, viral respiratory disease, asthma, depression, and scleroderma. See, e.g., Taylor P. C. et al Curr Pharm Des. 2003; 9(14): 1095-106; Dellinger R. P. et al Clin Infect Dis. 2003; 36(10): 1259-65; Takashiba S. et al J Periodontol. 2003; 74(1): 103-10; Diwan A. et al Curr Mol Med. 2003; 3(2): 161-82; Lundberg I. E. et al Rheum Dis Clin North Am. 2002; 28(4): 799-822; Makhija R. et al J Hepatobiliary Pancreat Surg. 2002; 9(4): 401-10; Chung K. F. et al Eur Respir J Suppl. 2001; 34:50s-59s; Hallegua D. S. et al Ann Rheum Dis. 2002; 61(11): 960-7; Goldring M. B. et al Expert Opin Biol Ther. 2001; 1(5): 817-29; Mrak R. E. et al Neurobiol Aging. 2001; 22(6): 903-8; Brady M. et al Baillieres Best Pract Res Clin Gastroenterol. 1999; 13(2): 265-89; Van der Meer J. W. et al Ann N Y Acad Sci. 1998; 856:243-51; Rameshwar P. et al Acta Haematol 2003; 109(1): 1-10; de Kozak Y et al Int Rev Immunol. 2002; 21(2-3): 231-53; Wang C. X. et al Prog Neurobiol. 2002; 67(2): 161-72; Van Reeth K. et al Vet Immunol Immunopathol. 2002; 87(3-4): 161-8; Stirling R. G. et al Br Med Bull. 2000; 56(4): 1037-53; Leonard B. E. et al Int J Dev Neurosci. 2001; 19(3): 305-12; Allan S. M. et al Ann N Y Acad Sci. 2000; 917:84-93; and Cafagna D. et al Minerva Med. 1998; 89(5): 153-61.

SUMMARY

This invention is based on a surprising discovery that an extract of Andrographis paniculata inhibits expression of both TNFα and IL-1β. The extract, obtained from the aerial part of Andrographis paniculata, contains andrographolide, 14-deoxy-andrographolide, 14-deoxy-11,12-dehydrogen-andrographolide, and neoandrographolide. Preferably, the extract contains 2-20% by weight andrographolide, 1-6% by weight 14-deoxy-andrographolide, 1-12% by weight 14-deoxy-11,12-dehydrogen-andrographolide, and 1-5% by weight neoandrographolide. More preferably, the extract contains 3-8% by weight andrographolide, 3-5% by weight 14-deoxy-andrographolide, 7-9% by weight 14-deoxy-11, 12-dehydrogen-andrographolide, and 2-4% by weight neoandrographolide. It is particularly preferred that the extract contain 4.2% by weight andrographolide, 4.4% by weight 14-deoxy-andrographolide, 8% by weight 14-deoxy-11,12-dehydrogen-andrographolide, and 2.1% by weight neoandrographolide.

One aspect of this invention relates to a method of inhibiting expression of TNFαor IL-1β in a subject. The method includes administering to the subject an effective amount of the above-described extract.

Another aspect of this invention relates to a method of treating a disorder related to TNFα or IL-1β, i.e., inflammatory bowel disease (including Crohn's disease and ulcerative colitis), chronic heart failure, diabetes mellitus, systemic lupus erythematosus, polymyositis/dermatomyositis, psoriasis, acute myelogenous leukemia, AIDS dementia complex, hematosepsis, septic shock, graft-versus-host disease, uveitis, asthma, acute pancreatitis, or periodontal disease. The method includes administering to a subject in need of the treatment an effective amount of the above-described extract.

Also within the scope of this invention is a composition containing the extract of this invention described above for use in treating TNFα related disorders and IL-1β related disorders as well as the use of such a composition for the manufacture of a medicament for treating these disorders.

Details of several embodiments of the invention are set forth in the description below. Other features, objects, and advantages of the invention will be apparent from the description, and also from the claims.

DETAILED DESCRIPTION

This invention includes methods of inhibiting expression of TNFα or IL-1β, treating a TNFα related-disorder, and treating an IL-1β-realted disorder by administering to a subject in need thereof an effective amount of the above-described extract. The term "an effective amount" refers to the amount of the extract which is required to confer one of the above-described effects in the subject. Effective amounts may vary, as recognized by those skilled in the art, depending on route of administration, excipient usage, and the possibility of co-usage with other agents. The term "treating" refers to administering the extract to a subject that has a TNFα related disorder or an IL-1β related disorder, or has a symptom of the disorder, or has a predisposition toward the disorder, with the purpose to cure, heal, alleviate, relieve, alter, remedy, ameliorate, improve, or affect the disorder, the symptoms of the disorder, or the predisposition toward the disorder.

To prepare an extract for use in this invention, one can immerse the aerial part of Andrographis paniculata in one or more suitable solvents, e.g., ethanol, methanol, and acetone; separate the liquid from the solid residue; and concentrate the liquid. The extract thus obtained may be further processed. For example, one can remove impurities or modify the ratio of the components by chromatography.

To practice one of the above-described methods, one administers to a subject in need thereof orally, rectally, parenterally, by inhalation spray, or via an implanted reservoir a composition that is either the above-mentioned extract alone or a mixture of the extract and a pharmaceutically acceptable carrier. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

An oral composition can be any orally acceptable dosage form including, but not limited to, tablets, capsules, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A sterile injectable composition (e.g., aqueous or oleaginous suspension) can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A topical composition can be formulated in form of oil, cream, lotion, ointment and the like. Suitable carriers for the composition include vegetable or mineral oils, white petrolatum (white soft paraffin), branched chain fats or oils, animal fats and high molecular weight alcohols (greater than C12). The preferred carriers are those in which the active ingredient is soluble. Emulsifiers, stabilizers, humectants and antioxidants may also be included as well as agents imparting color or fragrance, if desired. Additionally, transdermal penetration enhancers may be employed in these topical formulations. Examples of such enhancers can be found in U.S. Pat. Nos. 3,989,816 and 4,444,762. Creams are preferably formulated from a mixture of mineral oil, self-emulsifying beeswax and water in which mixture the active ingredient, dissolved in a small amount of an oil, such as almond oil, is admixed. An example of such a cream is one which includes about 40 parts water, about 20 parts beeswax, about 40 parts mineral oil and about 1 part almond oil. Ointments may be formulated by mixing a solution of the active ingredient in a vegetable oil, such as almond oil, with warm soft paraffin and allowing the mixture to cool. An example of such an ointment is one which includes about 30% almond and about 70% white soft paraffin by weight.

A carrier in a pharmaceutical composition must be "acceptable" in the sense of being compatible with the active ingredient of the formulation (and preferably, capable of stabilizing it) and not deleterious to the subject to be treated. For example, solubilizing agents, such as cyclodextrins (which form specific, more soluble complexes with one or more of active compounds of the extract), can be utilized as pharmaceutical excipients for delivery of the active compounds. Examples of other carriers include colloidal silicon dioxide, magnesium stearate, cellulose, sodium lauryl sulfate, and D&C Yellow #10.

A suitable in vitro assay can be used to preliminarily evaluate the efficacy of the above-described extract in inhibiting expression of TNFα or IL-10 expression. The extract can further be examined for its efficacy in treating a TNFα related disorder or an IL-1β related disorder by in vivo assays. For example, the extract can be administered to an animal (e.g., a mouse model) having a TNFα or IL-1β related disorder and its therapeutic effects are then accessed. Based on the results, an appropriate dosage range and administration route can also be determined.

Without further elaboration, it is believed that the above description has adequately enabled the present invention. The following specific examples are, therefore, to be construed as merely illustrative, and not limitative of the remainder of the disclosure in any way whatsoever. All of the publications, including patents, cited herein are hereby incorporated by reference in their entirety.

Preparation of an Extract of Andrographis paniculata

Dried powder of the aerial part of Andrographis paniculata (1 kg) was suspended in 85% ethanol. The suspension was refluxed for two hours and filtered. The residue was extracted with 85% ethanol again. The combined ethanol solutions were cooled and concentrated to afford 105 g of the desired extract. HPLC analysis shows that the extract contained 4.0% andrographolide.

In vitro Assay

An in vitro assay was conducted to evaluate the efficacy of the Andrographis paniculata extract in inhibiting expression of TNFα and IL-1β expression. Peripheral blood monocytes (PBMC) cells were isolated from fresh blood using the Ficoll-Paque Plus (Amersham Bioscience) according to the protocol recommended by the manufacturer. The cells were suspended in RPMI 1640 media containing 10% FBS at a concentration of $1\times10^5$ cells/ml and seeded in a 96-well plate ($1\times10^4$ cells total in each well). Each reaction was carried out in three wells.

10 μl of the Andrographis paniculata extract in DMSO was added into each well (final concentrations: 0.1, 0.3, 1, 3, 10, and 30 μg/ml). Wells containing dexamethason (CalBiochem.) at the final concentration of 10 μM were used as positive control. Wells containing 10 μl of the media were used as negative control. The plate was incubated at 37° C. under 5% $CO_2$ for 15 minutes. After 10 μl aliquots of 100 μg/ml lipopolysaccharide were added to all wells except for the negative control, the plate was incubated at 37° C. under 5% $CO_2$ overnight.

The plate was spun at 1000 rpm for 15 minutes and the supernatants were collected. Concentrations of TNFα and IL-1β were measured using the TNFα ELISA (Enzyme Linked Immunosorbent Assay) Kit and IL1-β ELISA Kit (Jingmei Bioengineer Technology).

The inhibition ratio was calculated as follows:

$$\text{Inhibition Ratio } (\%) = \left(1 - \frac{C_{extract} - C_{Control}}{C_{LPS} - C_{Control}}\right) \times 100$$

where $C_{extract}$ is the concentration of TNFα or IL-1β in PBMC cells treated with the extract and LPS, $C_{LPS}$ is the concentration of TNFα or IL-1β in PBMC cells treated with LPS and dexamethason, and $C_{Control}$ is the concentration of TNFα or IL-1β in PBMC cells without being treated with LPS or the extract.

The results show that the extract significantly inhibited expression of both TNFα and IL-1β.

In vivo Assays

In vivo assays were conducted to evaluate the efficacy of the Andrographis paniculata extract in treating inflammatory bowel disease (IBD).

Balb/c male mice (18-24 g) were anaesthetized with 1% pentobarbital sodium at 0.05 mg/10 g. To induce IBD, 1.5 mg of 2,4,6-trinitrobenzenesulfonic acid (TNBS; Sigma) in 50% ethanol was administered slowly to each mouse (except blank control mice) via a catheter. Blank control mice only received 0.1 ml of 50% ethanol. The mice were treated with the extract of Andrographis paniculata 24 hours and 2 hours prior to the TNBS administration and daily for 5 days after the administration.

The body weight of each mouse was monitored every day before and after the TNBS administration. The mice were sacrificed 24 hours after the last administration of the extract. Colons were removed and weighed. Furthermore, the colon weight to body weight ratio was calculated and adhesion between colon and other organs was also monitored.

Samples of colon tissues located precisely 2 cm above the anal canal were obtained, fixed in 10% buffered phosphate, embedded in paraffin, sectioned, and stained with hematoxylin/eosin. The degree of inflammation on microscopic cross sections was graded from 0 to 4 (0: no signs of inflammation; 1: a very low level of inflammation; 2: a low level of leukocyte infiltration; 3: a high level of leukocyte infiltration, a high vascular density, and a thickened colon wall; and 4: transmural infiltrations, loss of goblet cells, a high vascular density, and a thickened colon wall).

The results show that when mice were treated with 150 mg/kg TNBS alone, they had severe illness characterized by diarrhea, profound and sustained weight losses, a significant increase of the colon weight to body weight ratio, and a mortality rate of 50%. Macroscopic examination indicates that the colon of each of mice had transmural inflammation in all layers of the bowel wall. In contrast, when mice were treated with the extract of Andrographis paniculata (500 mg/kg/day) prior to the induction of IBD, they had a reduced overall mortality rate, less severe wasting syndrome, a lower colon weight to body weight ratio, and a lower IBD score. The bowel wall was sleek and was not adhesive with surrounding tissues.

In a separate assay, male Wistar rats were used to evaluate the efficacy of the Andrographis paniculata extract in treating IBD following a procedure similar to that described above. To induce IBD, the rats were administered with 2,4-dinitrobenzenesulfonic acid, instead of TNBS.

Similar results were obtained. Specifically, rats treated with the Andrographis paniculata extract had a reduced overall mortality rate, less severe wasting syndrome, a lower colon weight to body weight ratio, and a lower IBD score, compared with those not treated with the extract.

OTHER EMBODIMENTS

A number of embodiments of the invention have been described. Nevertheless, it will be understood that various modifications may be made without departing from the spirit and scope of the invention. Accordingly, other embodiments are also within the scope of the following claims.

What is claimed is:

1. A method of treating an inflammatory bowel disease in a subject in *recognized* need thereof, comprising administering to the subject an effective amount of an extract of Andrographispaniculata, wherein the extract contains 2-20% by weight andrographolide, 1-6% by weight 14-deoxy-andrographolide, [1-12] *1.0-7*% by weight 14-deoxy-11,12-dehydrogen-andrographolide, and 1-5% by weight neoandrographolide.

2. The method of claim 1, wherein the extract contains 3-8% by weight andrographolide, [3] *1*-5% by weight 14-deoxy-andrographolide, *1.0*-7[-9]% by weight 14-deoxy-11,12-dehydrogen-andrographolide, and 2-4% by weight neoandrographolide.

[3. The method of claim 2, wherein the extract contains 4.2% by weight andrographolide, 4.4% by weight 14-deoxy-andrograpliolide, 8% by weight 14-deoxy-11,12-dehydrogen-andrographolide, and 2.1% by weight neoandrographolide.]

4. The method of claim 1, wherein the inflammatory bowel disease is Crohn's disease.

5. The method of claim 1, wherein the inflammatory bowel disease is ulcerative colitis.

6. The method of claim 5, wherein the extract contains 3-8% by weight andrographolide, [3] *1*-5% by weight 14-deoxy-andrographolide, *1.0*-7[-9]% by weight 14-deoxy-11,12-dehydrogen-andrographolide, and 2-4% by weight neoandrographolide.

[7. The method of claim 6, wherein the extract contains 4.2% by weight andrographolide, 4.4% by weight 14-deoxy-andrographolide, 8% by weight 14-deoxy-11,12-dehydrogen-andrographolide, and 2.1% by weight neoandrographolide.]

*8. A method of treating an inflammatory bowel disease comprising administering to a patient in recognized need of such treatment an effective amount for treating of an extract of Andrographis paniculata, comprising: 2-20% by weight andrographolide, 1.0-7% by weight 14-deoxy-11,12-dehydrogen-andrographolide, and 1-5% by weight neoandrographolide.*

*9. A method of treating an inflammatory bowel disease comprising administering to a patient in recognized need of such treatment an effective amount for treating of an extract of Andrographis paniculata, comprising 2-20% by weight andrographolide, 14-deoxy-andrographolide, 1.0-7% by weight 14-deoxy-11,12-dehydrogen-andrographolide, and 1-5% by weight neoandrographolide.*

*10. The method of claim 8 wherein said inflammatory bowel disease is Crohn's disease.*

*11. The method of claim 8 wherein said inflammatory bowel disease is ulcerative colitis.*

*12. The method of claim 9 wherein said inflammatory bowel disease is Crohn's disease.*

*13. The method of claim 9 wherein said inflammatory bowel disease is ulcerative colitis.*

* * * * *